United States Patent [19]

Warriner

[11] Plant 4,848

[45] May 18, 1982

[54] ROSE PLANT 71-11223

[75] Inventor: William A. Warriner, Tustin, Calif.

[73] Assignee: Jackson & Perkins Company, Medford, Oreg.

[21] Appl. No.: 190,656

[22] Filed: Sep. 24, 1980

[51] Int. Cl.[3] ..... A01H 5/00

[52] U.S. Cl. ..... Plt./23

[58] Field of Search ..... Plt./23

*Primary Examiner*—Robert E. Bagwill

*Attorney, Agent, or Firm*—Klarquist, Sparkman, Campbell, Leigh, Whinston & Dellett

[57] ABSTRACT

A floribunda rose variety having pink-pale orange to near white, flat form flowers on upright branches, blooming in clusters and having a slight, fruity fragrance.

1 Drawing Figure

This present invention relates to a new and distinct variety of rose plant of the floribunda class which was originated by me by crossing the variety Golden Wave, U.S. Plant Pat. No. 2,105, with the variety Bridal Pink, U.S. Plant Pat. No. 2,851.

The primary objective of this breeding was to produce a new rose variety with a floribunda habit, usable as a garden variety with a color different than Bridal Pink. This objective was substantially achieved along with other desirable improvements as evidenced by the following unique combination of characteristics which are outstanding in the new variety and which distinguish it from its parents as well as from all other varieties of which I am aware:

1. An upright, branching plant habit bearing blooms in clusters.
2. An attractive, urn shaped bud of near white tinted with pink and pale orange.
3. Open blooms of near white, flat form when fully open.
4. A slight, fruity fragrance.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with the Royal Horticultural Society Colour Chart except where ordinary dictionary significance of color is indicated.

Parentage:
- *Seed parent.*—Golden Wave.
- *Pollen parent.*—Bridal Pink.

Classification:
- *Botanical.*—Rosa hybrid.
- *Commercial.*—Floribunda.

FLOWER

Observations made from specimens grown at Irvine, Calif., in August, 1980.

Blooming habit: Continuous.

Bud:
- *Size.*—$\frac{7}{8}$" to 1" when petals start to unfurl.
- *Form.*—Long, blunt top, urn shaped.
- *Color.*—When sepals first divide, near 36A to 36D; when quarter open, upper side of petals 36D to near white; lower side of petals 36A to White 158D with overlay color of Orange 27A.
- *Sepals.*—Color: outer surface Green 138B, with heavy shading of Red-Purple 59A; three appendaged sepals lightly appendaged; two unappendaged sepals hairy edged; all sepals edged with stipitate glands.
- *Receptacle.*—Color: Green 138B. Shape: funnel. Size: large. Surface: slightly hairy.
- *Peduncle.*—Length: short. Surface: prickly and glandular. Color: bronzy. Strength: stiff, erect.
- *Opening.*—Spiral.

Bloom:
- *Size.*—Large. Average open size 3" to 4".
- *Borne.*—Singly and in clusters. Clusters: flat.
- *Stems.*—Medium, strong.
- *Form.*—When first open, high centered. Permanence: flattens; outer petal edges slightly curled.
- *Petalage.*—Number of petals under normal conditions 35 to 40.
- *Color.*—Center of flower: upper side of petals Near White to Yellow-White 158D. Reverse side of petals Near Orange 27B. Base of petals Yellow 4A. General tonality from a distance White to Orange 27B.
- *Variegations.*—None.
- *Discoloration.*—General tonality at end of third day, White to Orange 27D.
- *Fragrance.*—Moderate, fruity.

Petals:
- *Texture.*—Thick.
- *Shape.*—Round.
- *Form.*—Tips slightly recurved.
- *Arrangement.*—Imbricated, petaloids in center few.
- *Persistence.*—Drop off cleanly.
- *Lastingness.*—On the plant, long. As cut flower, long.

Reproductive parts:
- *Anthers.*—Large. Color, yellow. Arrangement, regular around styles.
- *Filaments.*—Color: yellow.
- *Pollen.*—Lemon yellow.
- *Styles.*—Color: very pale green.
- *Stigmas.*—Color: red.

PLANT

Form: Bush.

Growth: Very vigorous, branching. Normal height at Irvine, Calif., 4 feet.

Foliage: Number of leaflets on normal mid-stem leaves, mostly 7.

*Size.*—Small.

*Quantity.*—Normal.

*Color.*—New foliage: Near Red Purple 59A. Old foliage: Near Green 137A.

Leaflets:

*Shape.*—Oval pointed.

*Texture.*—Leathery.

*Edge.*—Serrated, undulated.

*Serration.*—Single, small.

*Petiole.*—Rachis: color: reddish. Underside: prickles.

*Stipules.*—Long, bearded.

*Disease resistance.*—Resistant to mildew, blackspot under normal growing conditions at Irvine, Calif.

Wood:

*New wood.*—Color: reddish. Bark: smooth.

*Old wood.*—Color: green. Bark: smooth.

Prickles:

*Quantity.*—On main stalks from base, many. On laterals from stalk, many.

*Form.*—Broad base, long, straight.

*Color when young.*—Brown.

*Position.*—Irregular.

Small prickles:

*Quantity.*—On main stalks, none. On laterals, none.

I claim:

1. A new and distinct variety of rose plant of the floribunda class, substantially as herein shown and described, characterized particularly as to novelty by the unique combination of a branched, upright, but compact, plant bearing clusters of near white blooms.

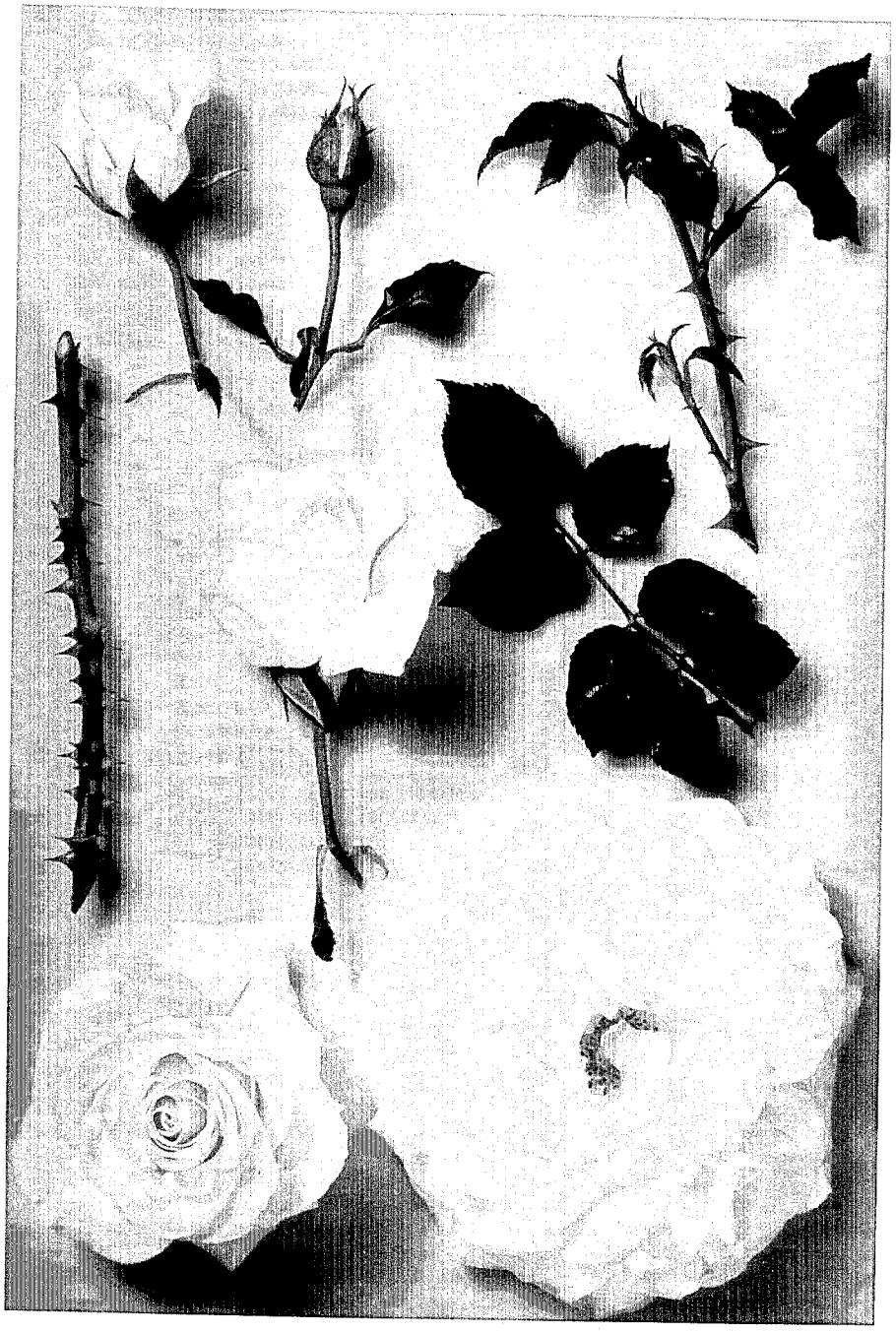

* * * * *